United States Patent
Wolniewicz

(10) Patent No.: US 10,803,466 B2
(45) Date of Patent: Oct. 13, 2020

(54) ANALYTIC MODELING OF PROTECTED HEALTH INFORMATION

(71) Applicant: 3M INNOVATIVE PROPERTIES COMPANY, St. Paul, MN (US)

(72) Inventor: Richard H. Wolniewicz, Longmont, CO (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 399 days.

(21) Appl. No.: 14/166,299

(22) Filed: Jan. 28, 2014

(65) Prior Publication Data

US 2015/0213458 A1    Jul. 30, 2015

(51) Int. Cl.
*G06Q 30/00* (2012.01)
*G16H 10/60* (2018.01)

(52) U.S. Cl.
CPC .......... *G06Q 30/018* (2013.01); *G16H 10/60* (2018.01)

(58) Field of Classification Search
CPC ........ G06Q 50/22; G06Q 50/24; G06Q 40/08; G06Q 10/10; G06F 19/322; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60;

(Continued)

(56) References Cited

U.S. PATENT DOCUMENTS 7,158,979 B2    1/2007    Iverson
7,269,578 B2    9/2007    Sweeney (Continued)

OTHER PUBLICATIONS

International Search Report for PCT International Application No. PCT/US2015/013005 dated May 7, 2015, 2 pages.

(Continued)

*Primary Examiner* — Michael Tomaszewski
*Assistant Examiner* — Mohmad Muqueeth
(74) *Attorney, Agent, or Firm* — Jonathan L. Tolstedt

(57) ABSTRACT

This disclosure includes techniques for analyzing patient data. In one example, a method includes accessing, by a computer system, one or more databases comprising health information for a plurality of patients, wherein the health information includes protected health information, randomly selecting, by the computer system, a subset of the health information from the one or more databases, wherein the subset of the health information corresponds to a subset of the plurality of patients, removing, by the computer system, the protected health information from the subset of health information to produce a de-identified analytics subset of patient data suitable for analytical model construction and evaluation, and storing, by the computer system, the de-identified analytics subset of the patient data in the one or more databases.

24 Claims, 6 Drawing Sheets

(58) Field of Classification Search
CPC ........ G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00
See application file for complete search history.

(56) References Cited

U.S. PATENT DOCUMENTS

| | | | |
|---|---|---|---|
| 7,376,677 | B2 | 5/2008 | Ober |
| 7,712,029 | B2 | 5/2010 | Ferreira |
| 7,823,207 | B2 | 10/2010 | Evenhaim |
| 7,865,376 | B2 | 1/2011 | Ober |
| 8,326,849 | B2 | 12/2012 | El Emam |
| 8,495,011 | B2 | 7/2013 | Sanders |
| 2002/0073099 | A1 | 6/2002 | Gilbert |
| 2006/0074983 | A1* | 4/2006 | Jones ............. G16H 10/65 |
| 2007/0055482 | A1 | 3/2007 | Goodermote et al. |
| 2007/0073811 | A1 | 3/2007 | Rubin |
| 2008/0147554 | A1 | 6/2008 | Stevens |
| 2008/0181396 | A1 | 7/2008 | Balakrishnana |
| 2008/0294459 | A1 | 11/2008 | Angell et al. |
| 2009/0043817 | A1 | 2/2009 | Sanders |
| 2010/0034376 | A1 | 2/2010 | Okuizumi |
| 2011/0010563 | A1 | 1/2011 | Lee |
| 2011/0077973 | A1 | 3/2011 | Breitenstein |
| 2011/0313790 | A1* | 12/2011 | Yao ................. G16H 50/50 705/3 |
| 2012/0060216 | A1 | 3/2012 | Chaudhri |
| 2012/0078659 | A1 | 3/2012 | Ashrafzadeh |
| 2012/0303616 | A1 | 11/2012 | Abuelsaad |
| 2013/0262142 | A1 | 10/2013 | Sethumadhavan |
| 2013/0263218 | A1 | 10/2013 | Awaraji et al. |
| 2013/0339053 | A1 | 12/2013 | Jacobs |

OTHER PUBLICATIONS

"National Institutes of Health—Clinical Research and the HIPAA Privacy Rule and Its Impacts on Research", [retrieved from the internet on Mar. 26, 2014], URL <http://privacyruleandresearch.nih.gov/clin_research.asp>, 20 pages.

"US Department of Health and Human Services—Health Information Privacy", Dec. 3, 2002, Revised Jun. 5, 2013, [retrieved from internet on Mar. 26, 2014], URL<http://www.hhs.dov/ocr/privacy/hipaa/understanding/special/research/index.html>, 3 pages.

Song, "Practical Techniques for Searches on Encrypted Data", Proceedings of the IEEE Symposium on Security and Privacy, May, 2000, pp. 44-55.

Stankiewicz, U.S. Appl. No. 61/904,213, "Systems and Methods for Obfuscating Data Using Obfuscation Table", filed Nov. 14, 2013.

Stankiewicz, U.S. Appl. No. 61/904,223, "Systems and Methods for Obfuscating Data Using Obfuscation Table", filed Nov. 14, 2013.

Wolniewicz, U.S. Appl. No. 14/166,364, Analytics on Protected Health Information, filed Jan. 28, 2014.

Office Action from U.S. Appl. No. 14/166,364, dated Jan. 7, 2016, 16 pp.

Final Office Action from U.S. Appl. No. 14/166,364, dated Jul. 22, 2016, 20 pp.

* cited by examiner

ANALYTIC MODELING OF PROTECTED HEALTH INFORMATION

TECHNICAL FIELD

This disclosure relates to techniques for analytic modeling of health information.

BACKGROUND

In the medical field, accurate processing of records relating to patient visits to hospitals and clinics ensures that the records contain reliable and up-to-date information for future reference. Accurate processing may also be useful for medical systems and professionals to receive prompt and precise reimbursements from insurers and other payers. Some medical systems may include electronic health record (EHR) technology that assists in ensuring records of patient visits and files are accurate in identifying information needed for reimbursement purposes. These EHR systems generally have multiple specific interfaces into which medical professionals may input information about the patients and their visits.

The patient files within the EHR usually include protected health information (PHI). PHI represents personal information to which limited access is desirable and often required by government laws and regulations, such as the Health Insurance Portability and Accountability Act of 1996 (HIPAA) and Health Information Technology for Economic and Clinical Health (HITECH) in the United States. Similar laws to restrict access to PHI exist in many other countries.

SUMMARY

In general, this disclosure describes techniques for analytic modeling of PHI in a way that can limit user access to the PHI. In this manner, the PHI can be sheltered from view by the user so as to ensure its protected status. Accordingly, the techniques may improve the ability to ensure privacy of patients, and may be useful for legal or regulatory compliance.

In one example, this disclosure is directed to a method for analyzing patient data. The method includes accessing, by a computer system, one or more databases comprising health information for a plurality of patients, wherein the health information includes protected health information, randomly selecting, by the computer system, a subset of the health information from the one or more databases, wherein the subset of the health information corresponds to a subset of the plurality of patients, removing, by the computer system, the protected health information from the subset of health information to produce a de-identified analytics subset of patient data suitable for analytical model construction and evaluation, and storing, by the computer system, the de-identified analytics subset of the patient data in the one or more databases.

In another example, this disclosure is directed to a computer system for storing and analyzing health information for a plurality of patients comprising one or more databases comprising health information for a plurality of patients, wherein the health information includes protected health information, and health information, for a randomly-selected subset of the plurality of patients within the protected health information removed for the randomly-selected subset of the plurality of patients, and a user interface that facilitates user access to health information for a randomly-selected subset of the plurality of patients within the protected health information removed for the randomly-selected subset of the plurality of patients for analytical model construction and evaluation.

In a further example, this disclosure is directed to a computer-readable storage medium comprising instructions that, when executed, cause a processor to access one or more databases comprising health information for a plurality of patients, wherein the health information includes protected health information, randomly select health information from the one or more databases corresponding to a subset of the plurality of patients, remove the protected health information from the health information corresponding to the randomly-selected subset of the plurality of patients to produce a de-identified analytics subset of patient data suitable for analytical model construction and evaluation, and store the updated de-identified analytics subset of patient data in the one or more databases.

In another example, this disclosure is directed to a method for analyzing patient data. The method includes accessing, by a computer system, one or more databases comprising health information, with protected health information, for a plurality of patients, accessing, by the computer system, an analytical model, and receiving, by the computer system via a user interface, instructions to apply the analytical model to health information for each of the plurality of patients. The protected health information is isolated from the user interface to restrict access to the protected health information. The method further includes applying, by the computer system, the analytical model to health information for each of the plurality of patients, and storing a result of the analytical model to the one or more databases.

In another example, this disclosure is directed to a computer system for storing and analyzing health information for a plurality of patients comprising one or more databases comprising health information, with protected health information, for a plurality of patients, a user interface, and a processor configured to apply an analytical model to patient data for each of the plurality of patients based on instructions received via the user interface, and storing a result of the analytical model to the one or more databases. The protected health information is isolated from the user interface to restrict access to the protected health information.

In a further example, this disclosure is directed to a computer-readable storage medium comprising instructions that, when executed, cause a processor to access one or more databases comprising health information, with protected health information, for a plurality of patients, receive, via a user interface, instructions to apply an analytical model to health information for each of the plurality of patients, apply the analytical model to health information for each of the plurality of patients, and store a result of the analytical model to the one or more databases. The protected health information is isolated from the user interface to restrict access to the protected health information.

The details of one or more examples of this disclosure are set forth in the accompanying drawings and the description below. Other features, objects, and advantages will be apparent from the description and drawings, and from the claims.

DETAILED DESCRIPTION

Figure 1:
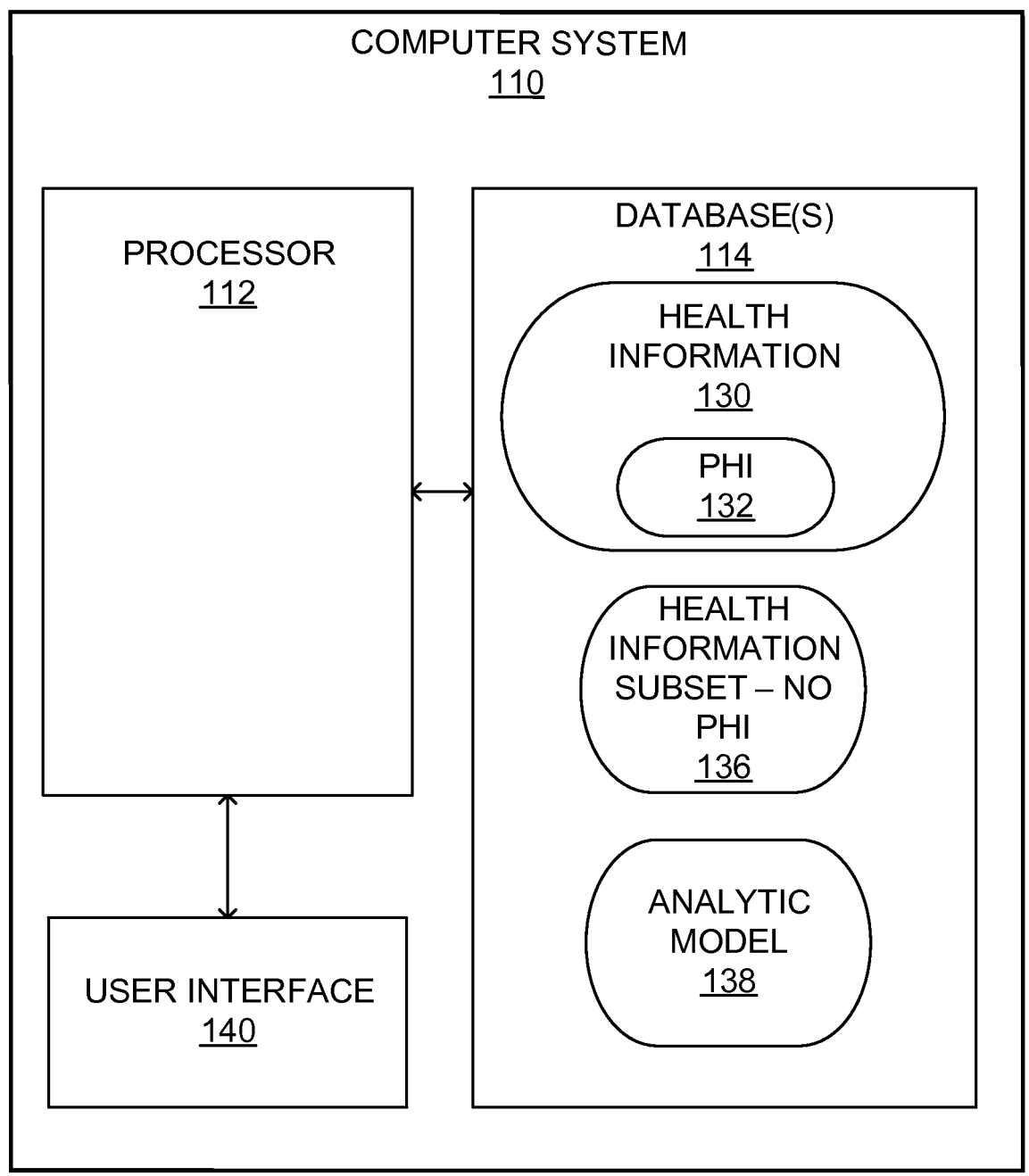
FIG. 1 is a block diagram illustrating an example of a computer system configured for analytic modeling of health information, such as health information including protected health information (PHI).

Healthcare may be improved through the application of big data analytics. As referred to herein, big data analytics refers to the use of statistical analytics in contexts where the data volume is very large, such as where the data volumes are so large that the volume itself is a problem. However, the analysis of healthcare information is greatly complicated by the need to limit access to protected health information (PHI) and satisfy the requirements of HIPAA and HITECH and similar laws and regulations across the globe. In particular, the use of big data analytics inherently requires analyzing very large quantities of data, and general big data techniques result in analysts viewing large subsets of the data, risking violating patient privacy laws, regulations, or causing other privacy concerns.

Patients may be asked to waive their privacy rights to produce significant quantities of data available for analytics, essentially bypassing the PHI restrictions. However, such techniques necessarily require a significant time investment to ask for patient waivers and then separate the patent data for which privacy rights have been waived before applying big data analytics to the patient data. In some cases, only a small fraction of patients are willing or can be reached to waive restrictions, which reduces the effectiveness of analytics as data volume is associated with accuracy.

In other examples, the entire data set, i.e., the patient data including PHI for all patients within a database may be located within a secured environment for applying big data analytics to the patient data. Under such examples, the system may rely on a surrounding "firewall" and assuming that those authorized to work within the firewall have unlimited access. However, such examples may create difficulties in compliance with patient privacy laws. Patient privacy laws may include requirements for logging user access to patient data and blocking access to data across healthcare systems. Another problem with such techniques is the common analytics practice of copying data as part of the analysis (e.g., download the data to another processor) for analytical model building and evaluation. Patient privacy laws often require careful tracking of where all of the copies of PHI are located and how and when they are accessed, and by whom. Compliance with these laws may be very difficult with data copied to files for analytics in general-purpose analysis engines.

Causes of PHI violations may occur with when those "other processors" are lost. Examples include laptops that go missing with PHI or even a hard drive on a copier that was disposed of without being wiped. Any time data moves out of the "secure" processors, there is a risk that all compliance monitoring is bypassed.

Furthermore, using a firewall for a group of patients within a database for a single healthcare institution may prevent combining data with other databases of patient data. This can limit the ability to develop analytical models as statistical analysis benefits greatly from increased data volumes, so further value can be derived from analytics across multiple providers than from any single provider. In particular, for every factor of four increase in data volumes, the standard error decreases by a factor of two.

In another example, patient data within a database may be de-identified or "anonymized" before making it available for analytics. However, such techniques may create difficulties with the data analysis. For example, some of the patient-identifying information may in fact be relevant to the development and application of analytical models, thus de-identified data may be potentially less effective to deliver value. As another example, there is no perfect solution for de-identifying unstructured data such as narrative text or images, though a substantial majority of all valuable healthcare data is in unstructured form.

These and other examples for enabling big data analytics while complying with patient privacy laws are disclosed herein. In general, the most valuable techniques for enabling big data analytics, while complying with patient privacy laws, attempt to utilize the large data volumes available for development and application of analytical models as well as mitigate the data quality issues associated with de-identification, and reduce the exposure of PHI to human analysts.

FIG. 1 is a block diagram illustrating an example of a computer system for analytic modeling of health information, such as health information including protected health information (PHI). Computer system 110 includes processor 112, at least one database 114, and user interface 140. Computer system 110 may also include other components and modules related to the processes described herein and/or other processes. In some examples, the components of computer system 110 may be distributed across one or more networks, such as a local area network (LAN) and/or the internet. The illustrated components are shown as one example, but other examples may be consistent with various aspects described herein.

User interface 140 may be configured to output information to a user or other device. For example, user interface 140 may include a display screen for presenting visual information to a user. In other examples, user interface 140 may include one or more different types of devices for presenting information to a user. Database 114 may comprise one or more memories or other storage units configured to store health information 130 for a plurality of patients, which may include data stored within documents such as patient medical records. Health information 130 includes PHI 132 for at least some of the plurality of patients. PHI 132 may be subject to patient privacy regulations.

Processor 112 may include a general-purpose microprocessor, a specially designed processor, an application specific integrated circuit (ASIC), a field programmable gate array (FPGA), a collection of discrete logic, and/or any type of processing device capable of executing the techniques described herein. In one example, database 114 may be configured to store program instructions (e.g., software instructions) that are executed by processor 112 to carry out the techniques described herein. In other examples, the techniques described herein may be executed by specifically programmed circuitry of processor 112. Processor 112 may thus be configured to execute the techniques described herein. Processor 112, or any other processes herein, may include one or more processors.

User interface 140 may include a display screen and/or include other types of output capabilities. For example, user interface 140 may include any number of visual (e.g., display devices, lights, etc.), audible (e.g., one or more speakers), and/or tactile feedback devices. In some examples, user interface 140 may represent both a display screen (e.g., a liquid crystal display or light emitting diode display) and a printer (e.g., a printing device or module for outputting instructions to a printing device). User interface 140 may be configured to allow users to view and select one or more medical documents from health information 130 for a plurality of patients, for example. User interface 140 may be configured to receive user input and communicate the user input to user interface 140, processor 112, and/or to database 114. User interface 140 may further be configured to receive user input to develop and/or apply analytical models to health information 130. The different components shown in FIG. 1 may be directly connected or interconnected, and in some examples, may use a data bus to facilitate communication between the components.

Health information 130 for a plurality of patients may include any information relating to interaction between patients and medical facilities or professionals. In some examples, health information 130 for a plurality of patients may also, or alternatively, include information collected or generated by medical device interaction with one or more patients. For example, during a visit to a facility or professional, a facility or medical professional may generate reports regarding a patient's health status, current treatments and outcomes, and/or results of any medical tests conducted for the patient. Generally, these medical documents may be grouped into a file identified as a health record for the specific patient. Each report may include multiple pages, portions, or sections, detailing the various aspects of the patient and/or the patient's visit. In some facilities, these patient health records may be kept as paper files. In some facilities, the paper records may be scanned and stored in a computer or computer memory as a digital health record that includes the medical documents.

In some examples, processor 112 may parse the medical documents or otherwise identify features or terms that may correspond to one or more medical codes. Processor 112 may then assign and output the generated one or more medical codes for each medical document to update health information within database 114.

Database 114 may further be configured to store health information subset 136, which does not include PHI. For example, health information subset 136 may represent a de-identified subset of data on which analytics can be performed to set up and test analytics programs, which will later be run against the complete data set with PHI. For example, by providing a statistically representative sample of health information without PHI within health information subset 136, an analyst may freely use that information to develop analytic models without the need to restrict access. However, by maintaining the original health information within health information 130, the analyst may test and apply the models developed using the de-identified subset of data, e.g., health information subset 136, to the full dataset of health information 130 including PHI 132.

In some examples, database 114 may further be configured to store analytic model 138. Analytic model 138 represents a program for analyzing health information such as health information 130 and/or health information subset 136. In some examples, processor 112 may receive instructions for the development and application of analytic model 138 via user interface 140. In various examples, computer system 110 may output a results summary of the application of analytic model 138 via user interface 140 and/or update health information 130 and/or health information subset 136 with the results of analytic model 138.

Database 114 includes one or more physically separate databases, e.g., stored in a memory. For example, health information 130 may be distributed across a number of physically separate computer systems. In some examples, the volume of health information 130 may be too large for a single server to store or process in a reasonable period of time. As an example, database 114 may include "NoSQL" database systems.

Likewise, processor 112 may also include one or more physically separate processors. For example, processing of health information 130 may be partitioned in parallel operations that are distributed to the same servers where the data partitions are stored, to limit data movement across network (s) connecting physically separate databases of database 114. As an example, processor 112 may incorporate Map-Reduce systems, such as Hadoop®.

As discussed in further detail below, processor 112 may apply one or more statistical operations and/or apply analytical models to health information 130. For example, processor may apply statistical operations, including sums, counts, means, medians, standard deviations, regressions, etc., through machine-learning techniques. Example machine-learning techniques include the construction of neural networks, decision tress, support vector machines, etc.

In addition to the techniques mentioned above for development and application of analytical models of health information, such as health information with PHI, discussed below are additional techniques that can be roughly described in six different categories. Note that any of the techniques below can be combined with one another and/or combined with the additional techniques discussed above. As mentioned above, in general, the most valuable techniques for enabling big data analytics while complying with patient privacy laws attempt to utilize the large data volumes available for development and application of analytical models as well as mitigate the data quality issues associated with de-identification, and reduce the exposure of PHI to human analysts.

A first category of techniques for development and application of analytical models of health information, such as health information with PHI, is combining the operational and analytics data storage to whatever extent possible. This limits persistent copies of data, reducing points of failure, and focusing logging and other regulatory infrastructure on a smaller number of functional points.

A second category of techniques for development and application of analytical models of health information, such as health information with PHI, is providing a de-identified subset of data on which analytics can be performed to set up and test the analytics programs, which will later be run against the complete data set with PHI. For example, by providing a statistically representative sample of health information without PHI, an analyst may freely use that information to develop analytic models without the need to restrict access. However, by maintaining the original health information, the analyst may test and apply the models developed using the de-identified subset of data, i.e., a subset of the health information with the PHI removed, to the full dataset of health information including the PHI.

A third category of techniques for development and application of analytical models of health information, such as health information with PHI, is providing the ability to view the analytics results on specific, tracked instances of PHI within the platform, so PHI does not need leave the platform even when the analyst must view the data to refine an analysis program. In this way, access to PHI, where necessary, is limited and may be logged for regulatory purposes.

A fourth category of techniques for development and application of analytical models of health information, such as health information with PHI, is providing the ability to submit an analytics program into the system, where it runs on the entire PHI, but output results are only statistical summaries viewable by the analyst. Patient privacy regulations such as HIPAA typically consider statistical summaries of data to be non-PHI where it is not possible to derive PHI for any particular patient from the data. In addition, at this stage, data may be filtered for right-to-use. That is, if some of the data includes personally identifying information, but the patient has waived the right to privacy, the analyst may be able to view the personally identifying information for patients that have waived the right to privacy.

A fifth category of techniques for development and application of analytical models of health information, such as health information with PHI, is providing the ability for analytic programs to be submitted to the system and run, limiting their outputs, which may include PHI, to production system uses where that PHI is legitimately usable to improve the care or other outcomes for the patient. For example, an analyst may run a model against health information for a multitude of patients, and then some of the patient files may be updated in accordance with the results of the model in a manner that restricts access to the PHI by the analyst.

A sixth category of techniques for development and application of analytical models of health information, such as health information with PHI, is tracking data right-to-use terms, and automatically filtering data for right-to-use. For example, analysts may designate the purpose of their analysis, which is then matched against individual data sets and their corresponding right-to-use terms.

These six categories of techniques for development and application of analytical models of health information, such as health information with PHI, as well as additional techniques for development and application of analytical models of health information are discussed in further detail below with respect to FIGS. 2-6.

Figure 2:
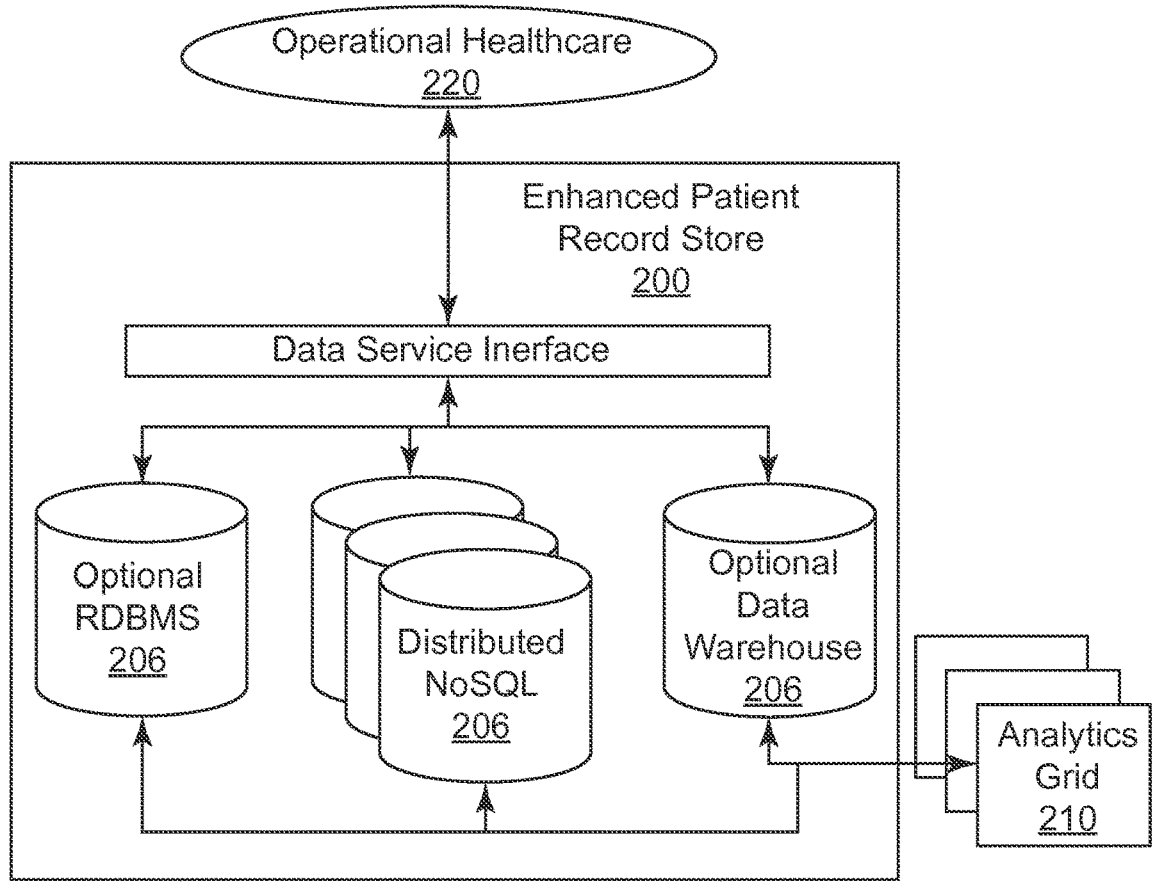
FIG. 2 is a conceptual illustration of a data service interface and the combined data storage system storing health information, such as health information including PHI.

FIG. 2 is a conceptual illustration of an enhanced patient record store 200, which provides a data service interface 202 and combined data storage system storing health information, such as health information including PHI. Enhanced patient record store 200 functions to combine operational data storage for operational healthcare system 220 and analytics data storage for analytics grid 210. Thus, enhanced patient record store 200 reduces the number of copies of health information data, which may reduce points of failure, and facilitate compliance with patient privacy regulations, e.g., by limiting the number of databases in which logging and other regulatory compliance infrastructure is required.

Health information, such as health information including PHI may be stored in a NoSQL distributed storage system 204. Optionally, enhanced patient record store 200 may duplicate portions of the data in a relational database system (RDBMS) 206 to perform transactional operations. Data may also be duplicated to data warehouse 208. For example, data warehouse 208 may implement a star schema and may support longitudinal analytics. Analytics grid 210 may run directly against the operational data, such as against NoSQL storage 204. In some examples, analytics jobs may be given lower priority than operational activities to limit the impact of analytics grid 210 on operational healthcare system 220.

In contrast to enhanced patient record store 200, other database systems may separate operational and analytic storage data storage. However, combining data storage for operational healthcare system 220 and analytics grid 210, as provided by enhanced patient record store 200, may provide one or more advantages to having separate database systems for operational and analytic healthcare information data storage.

As previously mentioned, combining data storage for operational healthcare system 220 and analytics grid 210 limits the number of databases in which logging and other regulatory compliance infrastructure is required. Combining data storage for operational healthcare system 220 and analytics grid 210 may also increase performance of both operational healthcare system 220 and analytics grid 210 by combining resources to produce a wider distribution of data across servers, increasing parallelism. In part, this may be achieved by using a NoSQL storage approach, minimizing or eliminating interfaces required to assemble a complete patient record. In addition, combining data storage for operational healthcare system 220 and analytics grid 210 may facilitate the ability to unify off-line analytics and operational analytics, e.g., the development of a potentially-preventable readmission (PPR) model and its deployment in production, without supporting multiple systems and multiple points of PHI-leakage risk.

In some examples, any or all of the components of enhanced patient record store 200 may be duplicated, in whole or in part, to isolate analytics grid 210 from operational healthcare system 220. In the same or different examples, NoSQL storage 204 may be eliminated. However, such modifications would lead to a system that includes additional copies of PHI, thus increasing the number of databases in which logging and other regulatory compliance infrastructure is required.

Figure 3:
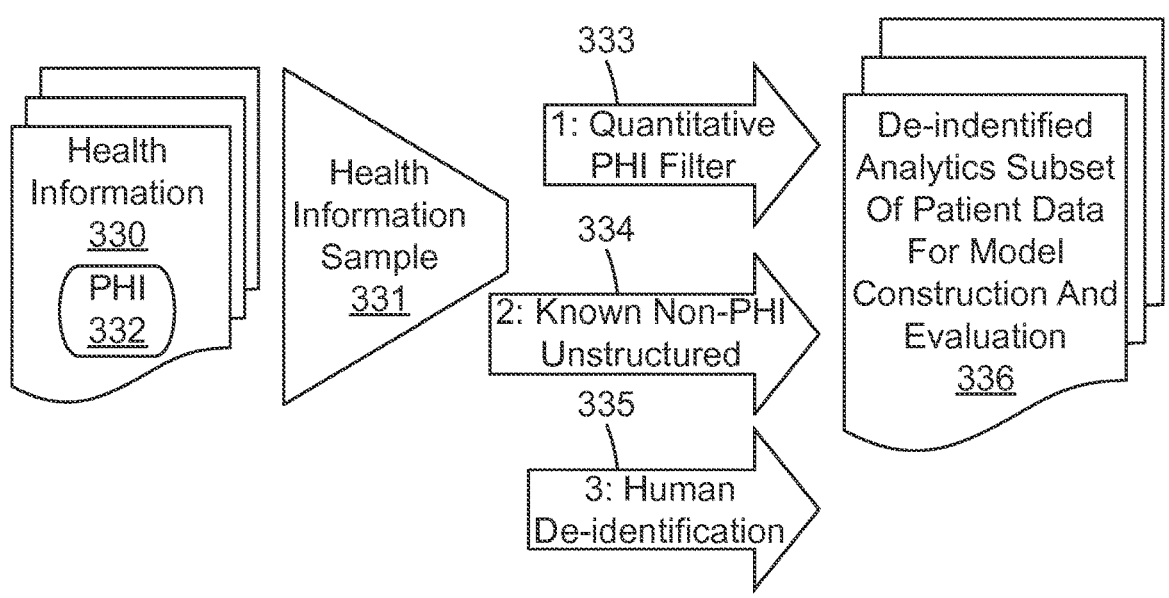
FIG. 3 illustrates example techniques for producing a de-identified analytics subset of patient data suitable for analytical model construction and evaluation.

FIG. 3 illustrates example techniques for producing a de-identified analytics subset of patient data 336 from health information 330, which includes PHI 332, suitable for analytical model construction and evaluation.

As illustrated in FIG. 3, a random sample of health information 331 is selected from health information 330. For example, the random sample of health information 331 may be associated with a random sample of patients associated with health information 330. The random sample of health information 331 is de-identified in that PHI is removed from the random sample of health information 331.

In particular, as illustrated in FIG. 3, the random sample of health information 331 may be de-identified according to three different processes. In other processes, additional or fewer techniques may be used to de-identify the random sample of health information 331.

In a first technique, quantitative PHI filter 333 may strip quantitative data from PHI fields within structured data, which are replaced with dummy values that cannot be reverse-engineered to derive the original data.

In a second technique, unstructured data will be pass filter 334, which retains only known anonymous data, such as general clinical concepts, phrases occurring in multiple patient records and the like. The unstructured data may be only a small subset of the data, but this technique may be valuable in that anonymity can be assured without human review. Examples techniques for filtering unstructured data are disclosed in U.S. Pat. App. No. 61/904,213, filed Nov. 14, 2013, entitled "Systems and Methods for Obfuscating Data Using Obfuscation Table" and U.S. Pat. App. No. 61/904,223, filed Nov. 14, 2013, entitled "Systems and Methods for Obfuscating Data Using Dictionary." The entire contents of each of these patent applications is incorporated by reference herein.

Additionally, unstructured data may be be de-identified by human reviewers 335, which may eliminate all references to identifiable information. De-identified analytics subset of patient data 336 results from health information sample 331 following processes 333, 334 and 335.

The techniques of FIG. 3 may be applied to a centralized database of health information such as database 114. In this manner, the techniques of FIG. 3 may be used by analysts to amortize the cost producing de-identified analytics subset of patient data 336 across multiple projects.

In the process of developing analytic models, analysts may find value in looking at some of the "raw" data to get a sense for how the data is structured, what kinds of features appear to be important, to diagnose errors in the model, or for other reasons. In environments where data access by analysts is not a concern, this may occur by quickly graphing or printing reports with subsets of the data, or paging through pages of unstructured data. However, in the case of health information including PHI, such as health information 330, providing unfettered access to PHI increased risk exposure to patient privacy violations from potentially viewing more data. The techniques of FIG. 3 allow de-identified analytics subset of patient data 336 to include as much health information as possible from health information sample 331 to aid analysts in the development and application of health information modeling.

As new patient data for existing patients is added to health information 330 in the normal course of application operations, if those patients are part of the random subset associated with health information sample 331, the new data may also be sent through processes 333, 334 and 335. In this manner, de-identified analytics subset of patient data 336 may be updated in conjunction to updates to health information sample 331.

In addition, as health information for new patients are added to health information 330, a random sample of the new patients may be added to health information sample 331, and that data may be sent through processes 333, 334 and 335. In this manner, de-identified analytics subset of patient data 336 may be updated in conjunction with new patients being added to health information 330.

The techniques of FIG. 3 may be applied to the full dataset of health information 130 (FIG. 1), including PHI 132, to create health information subset 136 (FIG. 1). For example, by providing a statistically representative sample of health information without PHI, such as health information subset 136 or de-identified analytics subset 336, an analyst may freely use that information to develop analytic models without the need to restrict access. However, by maintaining the original health information, such as health information 130 or health information 331, the analyst may test and apply the models developed using the de-identified subset of data, i.e., a subset of the health information with the PHI removed, to the full dataset of health information including the PHI.

The techniques of FIG. 3 provide a data set, de-identified analytics subset 336, against which general analytics can be performed and reduce the need to access or view PHI in the first place. The techniques of FIGS. 4-6 include the execution of models in an environment where the analyst does not have PHI access, even though the models may be executed against healthcare information that includes PHI.

In the normal course of most analytics activities, the full data set available for analysis exists in a place where the human analyst can freely view all of the data, both in its raw form, and as it is processed by the analytics model being developed. The default assumption necessary is that the human analyst may have viewed any of the raw data, despite the fact that the analyst can only practically view a small subset of a very large raw data set (typically millions, billions, or trillions of elements). Because the wide variety of low-level tools used to browse and analyze the data do not themselves do access tracking, it is not practical to log individual record access. This impracticality is acceptable in environments where the data is not sensitive in nature, such as a marketing researcher analyzing purchasing data for her company. However, with respect to health information that includes PHI, patient privacy regulations place restrictions on access to PHI as well as requirements for logging access to PHI.

Figure 4:
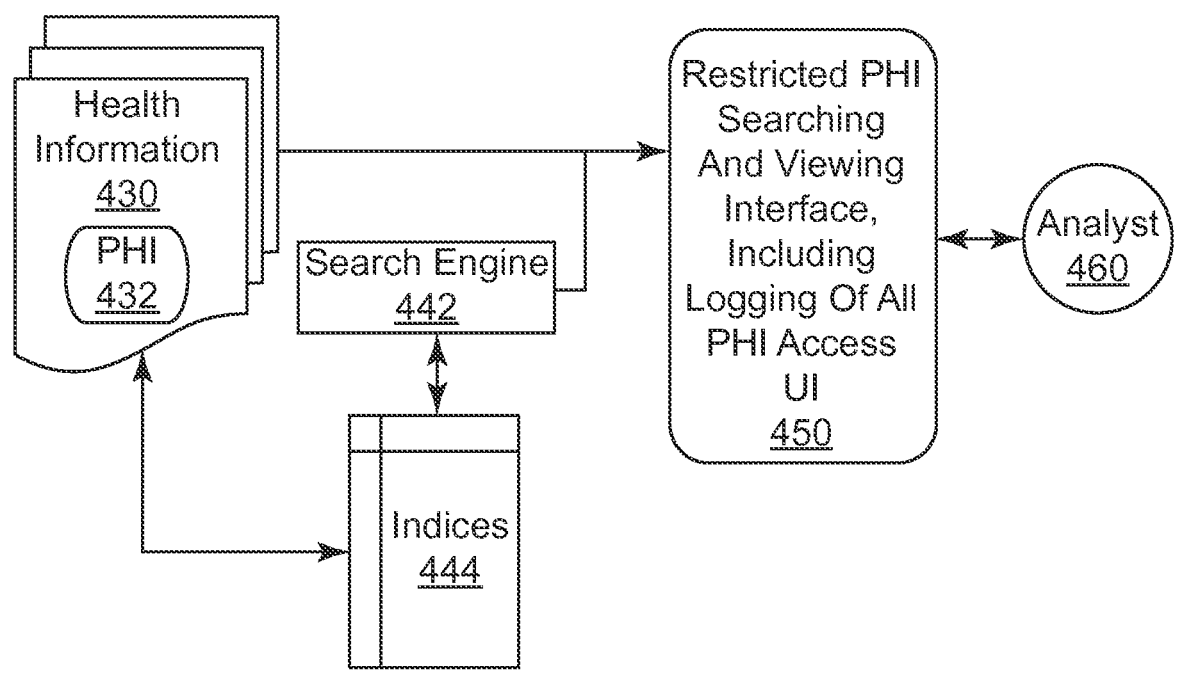
FIG. 4 is an operational diagram representing analyst interaction with a computer system that logs analyst access to PHI within the health information to facilitate compliance with patient privacy laws.

FIG. 4 is an operational diagram representing analyst interaction with a computer system that logs analyst access to PHI 432 within health information 430 to facilitate compliance with patient privacy regulations. The techniques of FIG. 4 provide analyst 460 the ability to view the analytics results on specific, tracked instances of PHI within the platform, so PHI does not need leave the platform even when the analyst must view the data to refine an analysis program. In this way, access to PHI, where necessary, is limited and easily logged for regulatory purposes.

As shown in FIG. 4, analyst 460 interacts with user interface 450 to apply and develop analytical models for health information 430, which includes PHI 432. The system of FIG. 4 provides a search engine 442 that allows analyst 460 to search for patients and documents matching specific criteria, where the resulting patients and documents are initially displayed in a list showing only de-identified information, such as obfuscated internal patient identifiers, details on which search terms resulted in hits, etc. Any indices on a data set with PHI is likely to include PHI, therefore the indices themselves are not visible to the user. By exposing the search capabilities through the user interface 450 and filtering the search results of PHI, the analyst can get the benefit of advanced search to identify specific records for review, minimizing the need for the analyst to page through data and therefore increase PHI exposure.

When analyst 460 accesses a particular patient record, the data may be presented as viewable to analyst 460, the internal markup of unstructured content is available, as is the results of any of the analysts' models already run against this data, so the analyst can interpret and refine models using user interface 450. However, user interface 450 does not provide any option for extracting PHI from the system via user interface 450. For example, the results of analyst request to accesses a particular patient record including PHI or otherwise view PHI may be presented as an image rather than HTML or other text that could be easily saved and processed via user interface 450. For example, user interface 450 may be a web browser.

In addition, the system of FIG. 4 may operate to log every access to PHI by analyst 460. In addition, the system of FIG. 4 may also further restrict access to PHI by analyst 460 based on the security authorization of the analyst.

Figure 5:
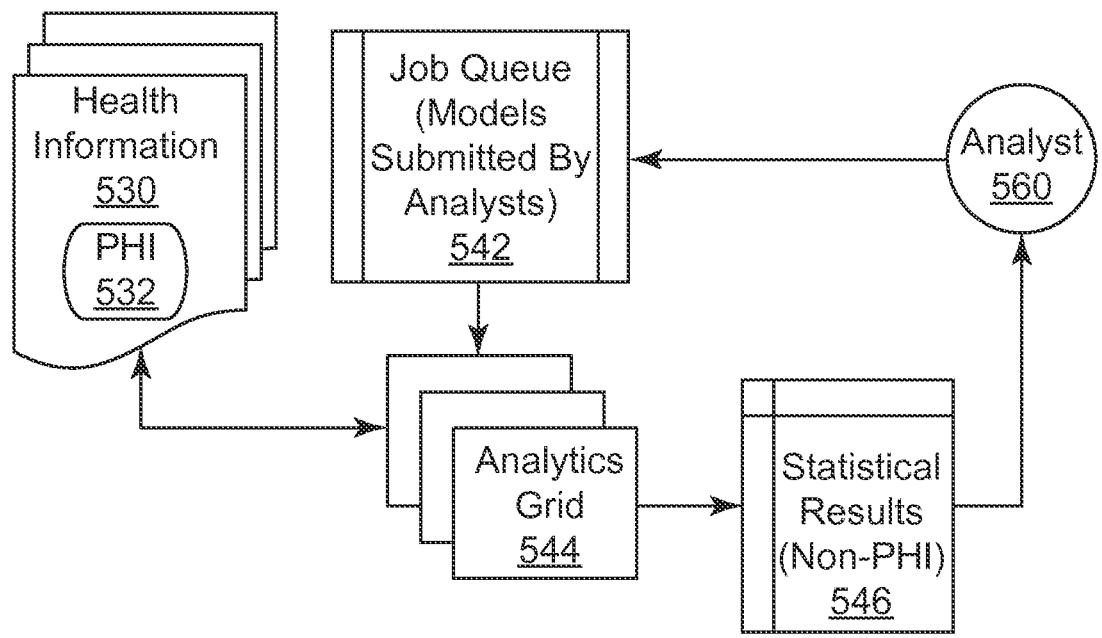
FIG. 5 is an operational diagram representing analyst interaction with a computer system that facilitates analytic modeling of health information while restricting analyst access to PHI within the health information.

FIG. 5 is an operational diagram representing analyst interaction with a computer system that facilitates analytic modeling of health information while restricting analyst access to PHI 532 within the health information 530. In particular, the techniques of FIG. 5 provide analyst 560 the ability to submit an analytics program, i.e., job queue 542, into the analytics grid 544, where it runs on the entire volume of health information 530, including PHI 532, but output results are only statistical summaries 546 viewable by the analyst. Statistical summaries 546 do not include PHI in that patient privacy regulations such as HIPAA typically consider statistical summaries of data to be non-PHI where it is not possible to derive PHI for any particular patient from the data. In addition, at this stage, data may be filtered for right-to-use. That is, if some of the data includes personally identifying information, but the patient has waived the right to privacy, the analyst may be able to view the personally identifying information for patients that have waived the right to privacy.

In this manner, analyst 560 submits a model to job queue 542, where the model has access to health information 530, including PHI 532, but analyst 560 does not have access to the models while they run against health information 530, including PHI 532. The models return statistical summaries 546, which in general are not considered PHI, and thus are returned to analyst 560. The exact content of model results returned to analyst 560 may be tracked and logged, so later audits can confirm that no PHI was accessed, exposed, or removed from the system.

In some examples, analytics grid 544 may include a large array of computational nodes, which may overlap with the servers storing health information 530, and health information 530 may be in NoSQL form. To preserve restricted access to PHI 532, analyst 560 does not have direct access to analytics grid 544. As one example, analytics grid 544 may be running map-reduce software such as Hadoop®, and/or may also run other statistical analysis software tools.

The data extracted from health information 530 may be filtered for right-to-use. In many cases, the statistical results 546 may be used in future models. For instance, a PPR model submitted might consist of the algorithms to generate features the analyst believes are indicative of PPR risk from patient records, along with an indicator of readmission. Using this set of input features and output target, a machine-learning algorithm is run to train a model such as a neural network or a support vector machine. The output of the run is the trained weights of the model; this itself is a new model that, in conjunction with the algorithms for input feature generation, can be used to analyze new patient records.

Figure 6:
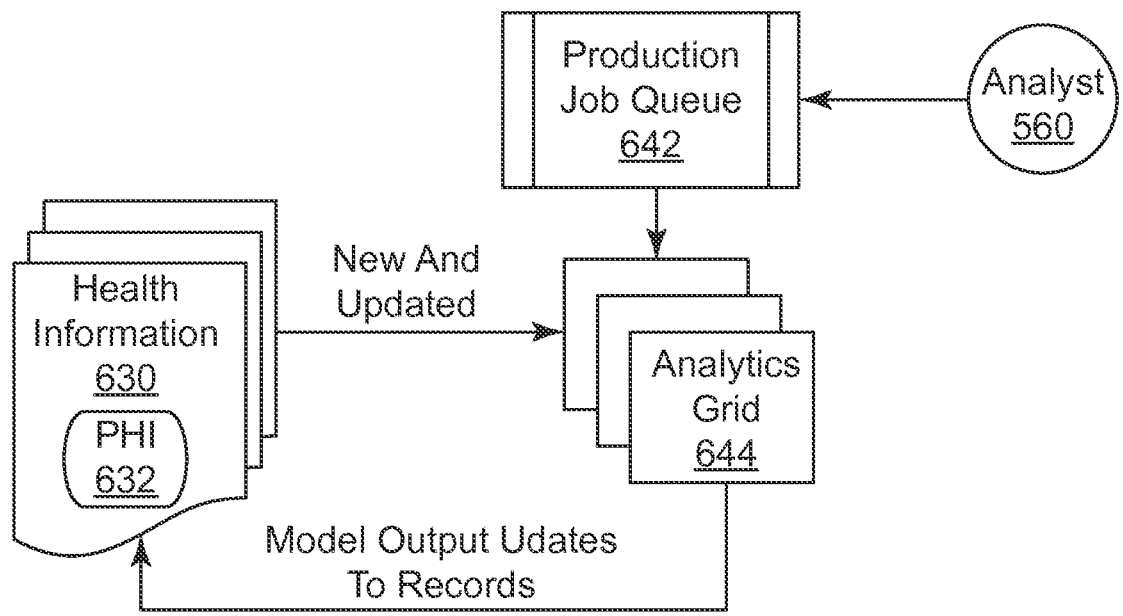
FIG. 6 is an operational diagram representing analyst interaction with a computer system that facilitates updating of health information associated with a plurality of patients while restricting analyst access to PHI within the health information.

FIG. 6 is an operational diagram representing analyst interaction with a computer system that facilitates updating of health information 630, which is associated with a plurality of patients while restricting analyst access to PHI 632 within the health information. The techniques of FIG. 6 allow analyst 660 the ability to submit analytic programs to production job queue 642 and run on analytics grid 644, limiting their outputs, which may include PHI, to production system uses, by updating or augmenting patient information within health information 630 according to the results of the analysis. The analyst does not need to see any PHI to effect the deployment of the analytic model to the operational environment. Updating or augmenting patient information within health information 630 is a legitimately use of PHI 632 to improve the care or other outcomes for the patient.

As an example, having built a model that analyst 660 believes meets the needs of a production application, analyst 660 may submits the model to production job queue 642 and run on analytics grid 644. The model may be automatically applied to new records within health information 630 with a frequency defined by analyst 660 within the model. For instance, analyst 660 might indicate that analytics grid 644 should run the model every night against new and changed patient records, and update or augment patient information within health information 630 according to the results of the nightly analysis. In this production process, there is no need for the analyst to access PHI 632.

In the same or different examples, data within health information 630 run through production models may be filtered to only those data sets where there is a right-to-use the data in the health information 630 for the modeled purpose. For example, analysts may designate the purpose of their analysis, which is then matched against individual data sets and their corresponding right-to-use terms. In many cases, this matching of data sets and corresponding rights-to-use terms may occur because a client has specifically contracted for the model results.

In some examples, the purpose of the model is specified. Such purposes may include modeling for products sold by a client, conducting strategic research on patterns in the data set, such as mentions of particular products, conditions, etc., supporting marketing activities, establishing specific norms and benchmarks, and conducting new model research for future products. Additional categories may be added in the future, and an analyst can add detail where needed, e.g., for new research, the particulars of the research, etc.

In the same or different examples, the set of clients, if any, for which a model is being run may also be specified. For example, a contract permitting access of health information may limit use of data to purposes specifically supporting the client.

For this reason, health information may be tagged with the source of the information, such as when a specific client is tagged as such. Some data may not be associated with a specific client, such as third party norms. In some examples, right-to-use information for data may include: products and activities where data use is allowed, products and activities where data use is disallowed, products and activities where data use is allowed if the activity is directly supporting the customer, and products and activities where data use is restricted in some other, contract-specific way.

Health information for analytic modeling may be filtered for the declared purpose of the model and for clients for which the model is to be applied. In addition, client data may have contract term for a particular modeling activity, or the client data may have a contracted term for modeling activity and the legal right to use has been established for this particular model against this client's data.

A second set of checks may be conducted prior to running a model, to prevent moving forward with any analytics until certain conditions are met. In such examples, for each data set (which may cover multiple clients), two items can be established. First that the set of legitimate uses of the data in terms of known modeling activities is defined. For instance, many PHI data sets may prohibit the use of data for marketing. As another example, user training or certification may be required before the data set can be used. For each analyst, the system may track (or access from an external training system) which training programs the analyst has completed, including expiration dates. An attempt to conduct an analysis against a data set for which the analyst has not completed necessary training may be blocked, with information about the required training provided back to the analyst.

EXAMPLE 1

By way of illustration consider the following example analysis to determine the risk for each of a plurality of patients for a "potentially preventable re-admission" or PPR. In this example, an analyst is trying to develop a statistical model to predict each patient's risk of re-admission, which is a significant driver of increased costs and is itself a lower-quality result for a patient.

Using the techniques disclosed herein, the analyst may access a computer system that combines operational and analytics data storage, such as that shown in FIG. 2. In this manner, the patient data for a plurality of patients is already being gathered in a system supporting hospital operations such as coding, and this same data storage is used as the basis for the PPR analytics.

The analyst may initially designate that their analysis relates to PPR, and before the analyst views data and before a model is trained or run against data, the data is filtered to only that data legitimately allowing PPR modeling. Thus, available health information may be filtered for right-to-use restrictions.

The analyst may develop an initial algorithm to train a PPR model from clinical data. The analyst may test the model on the de-identified subset to validate that the training algorithm is looking at the fields they expect to be relevant to the PPR analysis. Such a de-identified subset may be created in accordance with the techniques of FIG. 3.

Following the initial development of the model, the analyst may test whether proximity to the hospital is a factor in PPRs, and to do so wants to ensure addresses (a component of PHI) are being processed correctly. The analyst may submit a model to the system and accesses PHI within three patient records, confirming that the address is being properly handled. The records never leave the analytics system, the analyst's access of the three records is properly logged (along with its purpose), and the analyst is exposed to a minimal amount of PHI instead of the entire data set. Such techniques are also described more generally above with respect to FIG. 4.

Following further development of the model, the analyst may submit the debugged PPR model to the system to be trained using all available health information. Training may include: calculating regressions, computing neural network weights, and additional techniques. The model gets the benefit of all data (filtered for right-to-use for PPR models) in its training. The resulting statistics, showing which clinical record features combined with what weights to predict PPR probability, may be presented as a summary to the analyst, who can then refine and re-submit the model as needed. In accordance with the techniques of FIG. 5, the analyst does not need to access PHI when not necessary.

Having refined the model, the analyst may submit a final PPR model to production, to be run against all new patients going forward. For each patient, an individual PPR probability is produced and made available to the operational system and viewable by case managers, but not the original analyst. In accordance with the techniques of FIG. 6, health information may be updated without analyst access to PHI.

Thus, the example 1 illustrates how the techniques described with respect to FIGS. 2-6 may be combined to enabling big data analytics while complying with patient privacy laws and minimizing exposure of PHI as disclosed herein.

Figure 7:
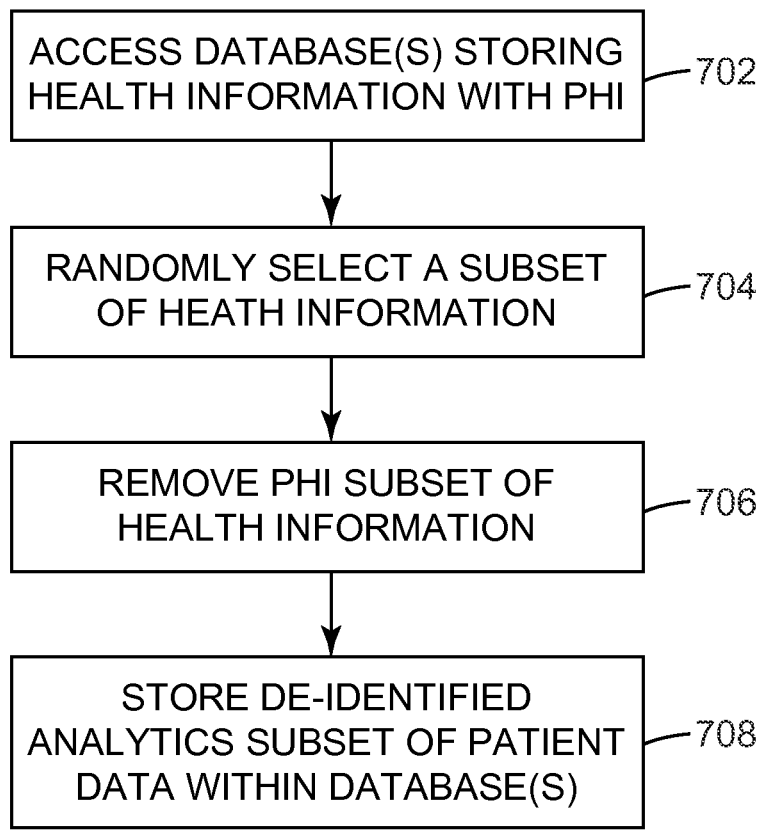
FIG. 7 is a flow diagram illustrating an example technique for producing a de-identified analytics subset of health information suitable for analytical model construction and evaluation.

FIG. 7 is a flow diagram illustrating an example technique for producing a de-identified analytics subset of health information suitable for analytical model construction and evaluation. For example, the techniques of FIG. 7 may be used to produce health information subset 136 (FIG. 1) or de-identified analytics subset of health information 336 of FIG. 3. For clarity, the techniques of FIG. 7 are discussed with respect to computer system 110 of FIG. 1.

First, processor 112 of computer system 110 accesses health information 130 within databases 114 for a plurality of patients (702). Health information 130 includes PHI 132.

Then, processor 112 randomly selects a subset of health information 130 from databases 114 (704). The subset of the health information corresponds to a subset of the plurality of patients.

Processor 112 then removes PHI from the subset of health information to produce a de-identified analytics subset of patient data 136 (706). De-identified analytics subset of patient data 136 is suitable for analytical model construction and evaluation. Removing the protected health information from the health information for the randomly-selected subset of the plurality of patients to produce the de-identified analytics subset of patient data suitable for analytical model construction and evaluation may include removing data from fields identified as including protected health information and filtering unstructured data to remove unstructured protected health information as described with respect to FIG. 3. Producing the de-identified analytics subset of patient data suitable for analytical model construction and evaluation may further comprise receiving, from a human user via user interface 140, indications of additional protected health information within the health information for the randomly-selected subset of the plurality of patients after removing the protected health information from the health information, and removing the additional protected health information indicated by the human user from the health information for the randomly-selected subset of the plurality of patients. Once produced, processor 112 may store de-identified analytics subset of the patient data 136 in databases 114 (708).

In some examples, processor 112 may present a representation of de-identified analytics subset of the patient data to a user via user interface 140 for analytical model construction and evaluation.

In addition, following an update to health information 130 within databases 114, the update including health information for additional patients, processor 112 may randomly select health information 130 corresponding to a subset of the additional patients. Processor 112 may remove PHI 132 from the health information for the randomly-selected subset of the additional patients and add the health information 130 for the randomly-selected subset of the additional patients without the removed protected health information to the de-identified analytics subset of patient data 136 to produce an updated de-identified analytics subset of patient data. Processor 112 may store the updated de-identified analytics subset of the patient data in databases 114.

In some examples, processor 112 may further receive an analytical model based on de-identified analytics subset of patient data 136, and apply the analytical model to health information 130 for the plurality of patients. For example, the analytical model may have been developed based on de-identified analytics subset of patient data 136 prior to its application to health information 130 for the plurality of patients. Processor 112 may output a summary of the results of the application of the analytical model to the health information with the protected health information for the plurality of patients via user interface 140. User interface 140 may restrict user access to the PHI 132, e.g., as described with respect to FIG. 5.

As another example, processor 112 may access an analytical model 138, which may be based on de-identified analytics subset of patient data 136, and apply analytical model 138 to health information 130 for the plurality of patients. For example, analytical model 138 may have been developed based on de-identified analytics subset of patient data 136 prior to its application to health information 130 for the plurality of patients. Processor 112 may compare the result of the application of analytical model 138 to the de-identified analytics subset of patient data 136 to a result of the application of the analytical model to the health information 130 for the plurality of patients, and present a summary of the comparison via user interface 140. User interface 140 may restrict user access to the PHI 132, e.g., as described with respect to FIG. 5 and FIG. 6.

In some examples, processor 112 may receive, from a human user via user interface 140, a request to access a portion of PHI 132 removed to produce de-identified analytics subset of patient data 136. In response to the request, processor 112 may present the requested protected health information to the human user via user interface 140, and store a record of the request to access the portion of PHI.

Figure 8:
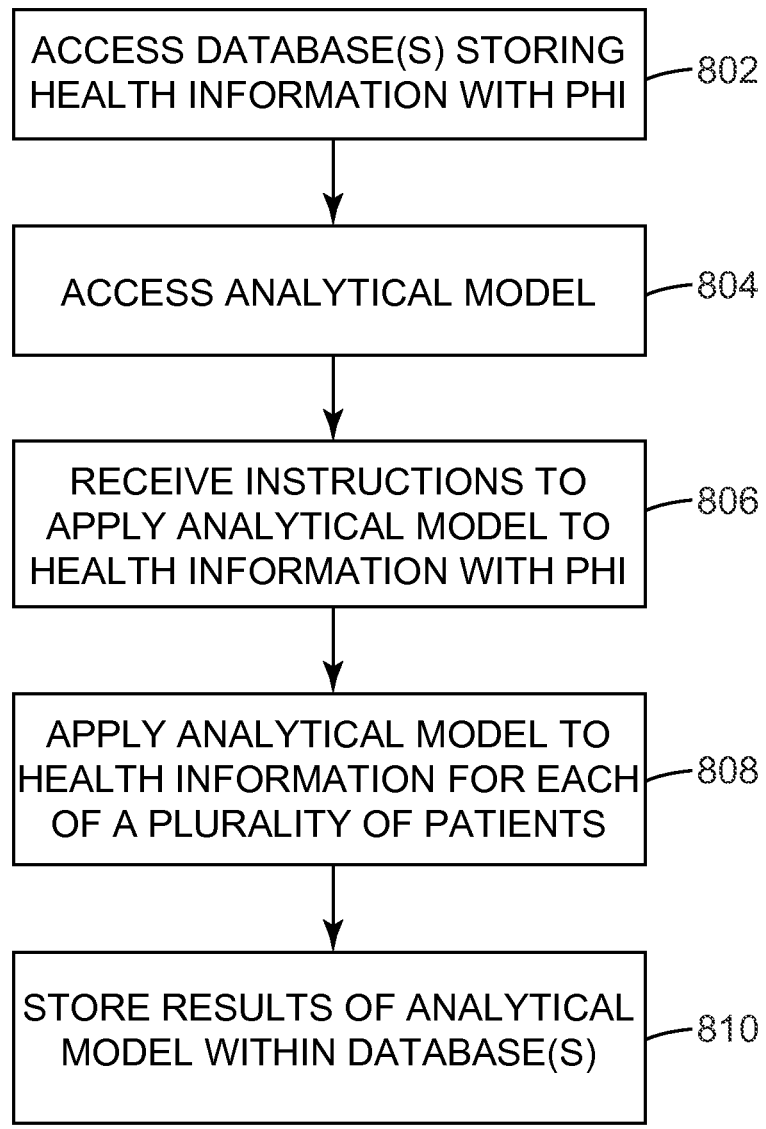
FIG. 8 is a flow diagram illustrating example techniques for analyzing health information associated with a plurality of patients while restricting access to PHI within the health information.

FIG. 8 is a flow diagram illustrating example techniques for analyzing health information associated with a plurality of patients while restricting access to PHI within the health information. For example, the techniques of FIG. 8 may generally correspond to the techniques described with respect to FIG. 5 and FIG. 6. For clarity, the techniques of FIG. 8 are discussed with respect to computer system 110 of FIG. 1.

First, processor 112 of computer system 110 accesses health information 130 within databases 114 for a plurality of patients (802). Health information 130 includes PHI 132. Processor 112 may also access analytical model 138 within databases 114 (804).

Processor 112 may receive instructions, via user interface 140, to apply analytical model 138 to health information 130 for each of the plurality of patients (806). PHI 132 is isolated from user interface 140 to restrict access to PHI 132. In some examples, health information 130 including PHI 132 may be isolated from user interface 140. Processor may apply model 138 to health information 130 for each of the plurality of patients (808). Processor may also store a result of the analytical model to databases 114 (810).

In some examples, processor 112 may present, via the user interface 140, a summary of the updated health information, wherein the summary of the updated health information excludes any of the protected health information. In some such examples, summary of the result of the analytical model may include statistical summary of health information resulting from the analytical model to facilitate user evaluation of the analytical model.

In the same or different examples, processor 112 may update health information 130 associated with at least some of the plurality of patients according to the results of the analytical model. For example, updating health information associated with at least some of the plurality of patients according to the results of the analytical model may include updating patient care information for at least some of the plurality of patients. As another example, updating health information associated with at least some of the plurality of patients according to the results of the analytical model include updating a patient health event risk assessment for at least some of the plurality of patients.

In some examples, processor 112 may receive, from a human user via user interface 140, a request to access a portion of PHI 132 removed to produce de-identified analytics subset of patient data 136. In response to the request, processor 112 may present the requested protected health information to the human user via user interface 140, and store a record of the request to access the portion of PHI.

The techniques of this disclosure may be implemented in a wide variety of computer systems, such as distributed computer systems, which may include any number of servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset.

If implemented in software, the techniques may be realized at least in part by a computer-readable storage medium comprising instructions that, when executed in a processor, performs one or more of the methods described above. The computer-readable storage medium may comprise a tangible computer-readable storage medium and may form part of a computer program product, which may include packaging materials. Example computer-readable storage media may include random access memory (RAM) such as synchronous dynamic random access memory (SDRAM), read-only memory (ROM), non-volatile random access memory (NVRAM), electrically erasable programmable read-only memory (EEPROM), FLASH memory, and magnetic or optical data storage media. The computer-readable storage medium may also comprise a non-volatile storage device, such as a hard disk, magnetic tape, a compact disk (CD), digital versatile disk (DVD), Blu-ray disk, holographic data storage media, or other non-volatile storage device. The computer-readable storage medium may be referred to as a non-transitory medium. The term "non-transitory" may indicate that the storage medium is not embodied in a carrier wave or a propagated signal. In certain examples, a non-transitory storage medium may store data that can, over time, change (e.g., in RAM or cache).

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

Various examples have been described. These and other examples are within the scope of the following claims.

What is claimed is:

1. A method for analyzing patient data, the method comprising:
accessing, by a computer system, one or more databases comprising health information for a plurality of patients, wherein the health information includes protected health information, the protected health information comprising personally identifiable information for each patient of the plurality of patients;
randomly selecting, by the computer system, a subset of the health information from the one or more databases, wherein the subset of the health information corresponds to a subset of the plurality of patients that comprises fewer patients than the plurality of patients, and wherein the subset of the health information comprises a subset of the protected health information corresponding to the subset of the plurality of patients;
removing, by the computer system, the subset of the protected health information from the subset of health information to produce a de-identified analytics subset of patient data suitable for analytical model construction and evaluation;
storing, by the computer system, the de-identified analytics subset of the patient data in the one or more databases;
limiting access by a human operator to the protected health information of the health information for the plurality of patients;
accessing, by the computer system, an analytical model comprising machine-learning algorithms for identifying features of interest in a health information dataset, the machine-learning algorithms comprising a neural network or a support vector machine and an initial set of algorithm weights;
applying, by the computer system, the analytical model to the de-identified analytics subset of the patient data to train the analytical model with the de-identified analytics subset of the patient data by generating first trained weights of the analytical model and modifying the analytical model by replacing the initial set of algorithm weights with the first trained weights; and
subsequent to applying the analytical model to the de-identified analytics subset, applying, by the computer system, the analytical model with the first trained weights to the health information that includes the protected health information for the plurality of patients to train the analytical model with the health information that includes the protected health information for the plurality of patients by generating second trained weights of the analytical model and modifying the analytical model by replacing the first trained weights with the second trained weights.

2. The method of claim 1, further comprising: presenting, by the computer system, the de-identified analytics subset of the patient data via a user interface for construction and evaluation of the analytical model.

3. The method of claim 1, further comprising outputting, by the computer system, a summary of the results of the application of the analytical model to the health information with the protected health information for the plurality of patients via a user interface restricting user access to the protected health information.

4. The method of claim 1, further comprising:
accessing, by the computer system, a result of the of the application of the analytical model to the de-identified analytics subset of patient data;
comparing, by the computer system, the result of the of the application of the analytical model to the de-identified analytics subset of patient data to a result of the of the application of the analytical model to the health information for the plurality of patients; and
presenting, by the computer system, a summary of the comparison of the result of the of the application of the analytical model to the de-identified analytics subset of patient data with the result of the of the application of the analytical model to the health information for the plurality of patients via a user interface restricting user access to the protected health information to facilitate evaluation of the suitability of the analytical model for the health information for the plurality of patients.

5. The method of claim 1, wherein removing, by the computer system, the subset of the protected health information from the subset of health information for the randomly-selected subset of the plurality of patients to produce the de-identified analytics subset of patient data suitable for analytical model construction and evaluation comprises, for each patient of the subset of the plurality of patients:
removing data from fields identified as including protected health information, wherein removing data comprises removing quantitative data from fields within structured data and replacing the removed quantitative data with dummy values; and
filtering unstructured data to remove unstructured protected health information and leave unstructured non-protected health information as part of the de-identified analytics subset.

6. The method of claim 1, wherein producing the de-identified analytics subset of patient data suitable for analytical model construction and evaluation further comprises:
receiving, from a human user, indications of additional protected health information within the health information for the randomly-selected subset of the plurality of patients after removing, by the computer system, the subset of the protected health information from the subset of the health information; and
removing, by the computer system, the additional protected health information indicated by the human user from the health information for the randomly-selected subset of the plurality of patients.

7. The method of claim 1, further comprising:
receiving, from a human user, a request to access the subset of the protected health information removed to produce the de-identified analytics subset of patient data;
presenting the requested protected health information to the human user; and
storing a record of the request to access the protected health information.

8. The method of claim 1, further comprising:
following an update to the one or more databases comprising health information for the plurality of patients, the update including health information for additional patients, randomly selecting, by the computer system, health information from the one or more databases of a subset of the additional patients;
removing, by the computer system, the protected health information from the health information for the randomly-selected subset of the additional patients;
adding the health information for the randomly-selected subset of the additional patients without the removed protected health information to the de-identified analytics subset of patient data to produce an updated de-identified analytics subset of patient data; and storing, by the computer system, the updated de-identified analytics subset of the patient data in the one or more databases.

9. A computer system for storing and analyzing health information for a plurality of patients comprising:

one or more databases comprising:

health information for a plurality of patients, wherein the health information includes protected health information, wherein the protected health information comprises personally identifiable information for each patient of the plurality of patients; and health information for a randomly-selected subset of the plurality of patients with the protected health information removed for the randomly-selected subset of the plurality of patients, the randomly-selected subset of the plurality of patients comprising fewer patients than the plurality of patients;

a user interface that facilitates, for analytical model construction and evaluation, user access to the health information for the randomly-selected subset of the plurality of patients with the protected health information removed for the randomly-selected subset of the plurality of patients, and limits access to the protected health information of the health information for the plurality of patients; and one or more processors configured to:

access, via the user interface, an analytical model comprising machine-learning algorithms for identifying features of interest in a health information dataset, the machine-learning algorithms comprising a neural network or a support vector machine and an initial set of algorithm weights;

apply the analytical model to the health information for the randomly-selected subset of the plurality of patients with the protected health information removed to train the analytical model with the de-identified analytics subset of the patient data by generating first trained weights of the analytical model and modifying the analytical model by replacing the initial set of algorithm weights with the first trained weights; and subsequent to applying the analytical model to the health information for the randomly-selected subset of the plurality of patients with the protected health information removed, apply the analytical model with the first trained weights to the health information that includes the protected health information for the plurality of patients to train the analytical model with the health information that includes the protected health information for the plurality of patients by generating second trained weights of the analytical model and modifying the analytical model by replacing the first trained weights with the second trained weights.

10. The computer system of claim 9, wherein the computer system is configured to output a summary of the results of the application of the analytical model to the health information with the protected health information for the plurality of patients via the user interface restricting user access to the protected health information.

11. The computer system of claim 9, wherein the one or more processors are configured to compare a result of the of the application of the analytical model to the health information for the randomly-selected subset of the plurality of patients with the protected health information removed to a result of the of the application of the analytical model to the health information for the plurality of patients; and wherein the computer system is configured to output a summary of the comparison of the result of the of the application of the analytical model to the health information for the randomly-selected subset of the plurality of patients with the protected health information removed with the result of the of the application of the analytical model to the health information for the plurality of patients via the user interface restricting user access to the protected health information.

12. The computer system of claim 9, further comprising one or more processors configured to remove the protected health information for the randomly-selected subset of the plurality of patients from the health information for the randomly-selected subset of the plurality of patients to produce the health information for the randomly-selected subset of the plurality of patients with the protected health information removed suitable for analytical model construction and evaluation.

13. The computer system of claim 9, wherein the one or more processors are configured to remove the protected health information from the health information for the randomly-selected subset of the plurality of patients to produce the health information for the randomly-selected subset of the plurality of patients with the protected health information removed according to steps including, for each patient of the randomly-selected subset of the plurality of patients:

removing data from fields identified as including protected health information, wherein removing data comprises removing quantitative data from fields within structured data and replacing the removed quantitative data with dummy values; and filtering unstructured data to remove unstructured protected health information and leave unstructured non-protected health information as part of the de-identified analytics subset.

14. The computer system of claim 9, wherein the one or more processors are configured to remove the protected health information from the health information for the randomly-selected subset of the plurality of patients to produce the health information for the randomly-selected subset of the plurality of patients with the protected health information removed according to steps including:

receiving, from a human user, indications of additional protected health information within the health information for the randomly-selected subset of the plurality of patients after removing, by the computer system, the protected health information from the health information for the randomly-selected subset of the plurality of patients; and removing the additional protected health information indicated by the human user from the health information for the randomly-selected subset of the plurality of patients.

15. The computer system of claim 9, wherein upon receipt of a request to access protected health information from the randomly-selected subset of the plurality of patients removed to produce the health information for the randomly-selected subset of the plurality of patients with the protected health information removed via the user interface, the computer system is configured to:

present the requested protected health information via the user interface; and store a record of the request to access the protected health information in the one or more databases.

16. The computer system of claim 9, wherein following an update to the one or more databases comprising health information for the plurality of patients, the update including health information for additional patients, the computer system is configured to:
   randomly select, from the one or more databases, health information of a subset of the additional patients;
   remove the protected health information from the health information corresponding to the randomly-selected subset of the additional patients;
   add the health information corresponding to the randomly-selected subset of the additional patients without the removed protected health information to the health information for the randomly-selected subset of the plurality of patients with the protected health information removed to produce an updated de-identified analytics subset of patient data; and
   store the updated health information for the randomly-selected subset of the plurality of patients with the protected health information removed in the one or more databases.

17. A non-transitory computer-readable storage medium comprising instructions that, when executed, cause one or more processors to:
   access one or more databases comprising health information for a plurality of patients, wherein the health information includes protected health information, the protected health information comprising personally identifiable information for each patient of the plurality of patients;
   randomly select a subset of the health information from the one or more databases corresponding to a subset of the plurality of patients that comprises fewer patients than the plurality of patients, and wherein the subset of the health information comprises a subset of the protected health information corresponding to the subset of the plurality of patients;
   remove the subset of the protected health information from the health information corresponding to the randomly-selected subset of the plurality of patients to produce a de-identified analytics subset of patient data suitable for analytical model construction and evaluation;
   store the de-identified analytics subset of patient data in the one or more databases;
   limit access by a human operator to the protected health information of the health information for the plurality of patients;
   access an analytical model comprising machine-learning algorithms for identifying features of interest in a health information dataset, the machine-learning algorithms comprising a neural network or a support vector machine and an initial set of algorithm weights;
   apply the analytical model to the de-identified analytics subset of the patient data to train the analytical model with the de-identified analytics subset of the patient data by generating first trained weights of the analytical model and modifying the analytical model by replacing the initial set of algorithm weights with the first trained weights; and
   subsequent to applying the analytical model to the de-identified analytics subset, apply the analytical model with the first trained weights to the health information that includes the protected health information for the plurality of patients to train the analytical model with the health information that includes the protected health information for the plurality of patients by generating second trained weights of the analytical model and modifying the analytical model by replacing the first trained weights with the second trained weights.

18. The non-transitory computer-readable storage medium of 17, further comprising instructions that, when executed, cause the one or more processors to present, via a user interface, the de-identified analytics subset of patient data for construction and evaluation of the analytical model.

19. The non-transitory computer-readable storage medium of claim 17, comprising further instructions that, when executed, cause the one or more processors to output a summary of the results of the application of the analytical model to the health information that includes the protected health information for the plurality of patients to a user via the user interface restricting user access to the protected health information.

20. The non-transitory computer-readable storage medium of claim 17, comprising further instructions that, when executed, cause the one or more processors to:
   access a result of the of the application of the analytical model to the de-identified analytics subset of patient data;
   compare the result of the of the application of the analytical model to the de-identified analytics subset of patient data to a result of the of the application of the analytical model to the health information for the plurality of patients; and
   present a summary of the comparison of the result of the of the application of the analytical model to the de-identified analytics subset of patient data with the result of the of the application of the analytical model to the health information for the plurality of patients to a user via the user interface restricting user access to the protected health information to facilitate evaluation of the suitability of the analytical model for the health information for the plurality of patients.

21. The non-transitory computer-readable storage medium of claim 17, wherein in removing the subset of the protected health information from the subset of health information for the randomly-selected subset of the plurality of patients to produce the de-identified analytics subset of patient data suitable for analytical model construction and evaluation, the instructions cause the one or more processors to, for each patient of the subset of the plurality of patients:
   remove data from fields identified as including protected health information, wherein removing data comprises removing quantitative data from fields within structured data and replacing the removed quantitative data with dummy values; and
   filter unstructured data to remove unstructured protected health information and leave unstructured non-protected health information as part of the de-identified analytics subset.

22. The non-transitory computer-readable storage medium of claim 17, wherein in producing the de-identified analytics subset of patient data suitable for analytical model construction and evaluation further the instructions cause the one or more processors to:
   receive, via a user interface, indications of additional protected health information within the health information for the randomly-selected subset of the plurality of patients after removing the subset of the protected health information from the subset of the health information; and remove the indicated additional protected health information from the health information for the randomly-selected subset of the plurality of patients.

23. The non-transitory computer-readable storage medium of claim 17, comprising further instructions that, when executed, cause the one or more processors to:
- receive, via the user interface, a request to access the subset of the protected health information removed to produce the de-identified analytics subset of patient data;
- present the requested protected health information via the user interface; and
- store a record of the request to access the protected health information.

24. The non-transitory computer-readable storage medium of claim 17, comprising further instructions that, when executed, cause the one or more processors to:
- follow an update to the one or more databases comprising health information for the plurality of patients, the update including health information for additional patients, randomly selecting health information from the one or more databases of a subset of the additional patients;
- remove the protected health information from the health information for the randomly-selected subset of the additional patients;
- add the health information for the randomly-selected subset of the additional patients without the removed protected health information to the de-identified analytics subset of patient data to produce an updated de-identified analytics subset of patient data; and
- present a representation the updated de-identified analytics subset of patient data via the user interface restricting user access to the protected health information for analytical model construction and evaluation.

* * * * *